United States Patent [19]

Ward

[11] Patent Number: 4,515,169

[45] Date of Patent: May 7, 1985

[54] DIFFERENTIAL LATENCY AUDIOMETER

[75] Inventor: John W. Ward, Charlottesville, Va.

[73] Assignee: Teledyne Industries, Inc., Los Angeles, Calif.

[21] Appl. No.: 433,641

[22] Filed: Oct. 12, 1982

[51] Int. Cl.³ .............................................. A61B 5/12
[52] U.S. Cl. ................................ 128/746; 179/107 R; 73/585
[58] Field of Search .................... 128/746, 731–733, 128/421, 422; 179/1 N; 73/585

[56] References Cited

U.S. PATENT DOCUMENTS

| 4,201,225 | 5/1980 | Bethea, III et al. | 128/746 |
| 4,327,252 | 4/1982 | Tumatis | 73/585 |
| 4,390,748 | 6/1983 | Zwicker | 73/585 |

OTHER PUBLICATIONS

"Essentials of Clinical Electric Response Audiometry", Gibson, 1978.
R. Nilsson & G. Liden, "Sound Localization with Phase Audiometry", Actua Otolaryngol 81:291–299, 1976, University of Goteborg, Goteborg, Sweden.
"Brain-Stem Electric Response Audiometry", J. Ward, Jun., 1981, vol. 34, No. 8, Hearing Aid Journal.
"Electric Response Audiometer"-TA–1000, Brochure #TA–1081, Teledyne Avionics, Charlottesville, Virginia.
"Electric Response Audiometer"-Model TA–1000, Designation No. SLZ9793C.
"Brainstem and Other Auditory Evoked Potentials, Principles, Techniques and Applications", Teter et al.

Primary Examiner—Lee S. Cohen
Assistant Examiner—Steven Falk
Attorney, Agent, or Firm—Cushman, Darby & Cushman

[57] ABSTRACT

An apparatus and a method for performing differential interaural latency evaluation utilizes the ability of the human brain to locate a complex sound source. Respective stimuli are simultaneously applied to the ears of the subject. The stimulus applied to one ear is offset in time with respect to the stimulus applied to the other ear. The stimuli are perceived by the subject as being generated by a sound source inside of the subject's head at a location within the head in accordance with the interaural differential latency. The relative time offset between the stimuli can be varied until the apparent source of the stimuli is perceived by the subject as being in the vicinity of a predetermined position. The time offset is ascertained and used to generate indicia of interaural differential latency, which is displayed by an electronic display.

41 Claims, 3 Drawing Figures

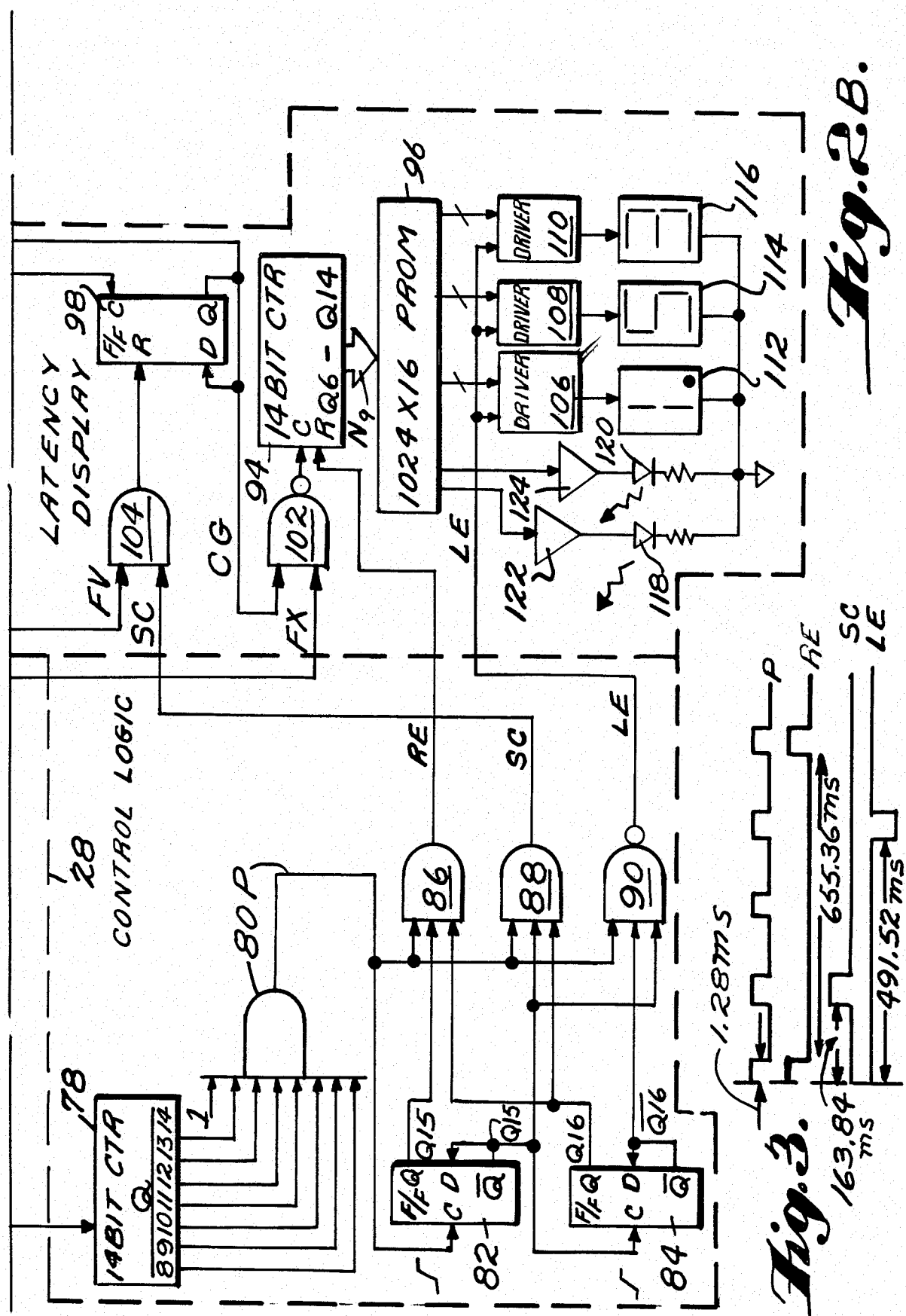

DIFFERENTIAL LATENCY AUDIOMETER

BACKGROUND OF THE INVENTION

The present invention relates to medical diagnostic apparatus, and in particular, to brain-stem electric response audiometry.

Brain-stem electric response audiometry (BSER) is a clinical technique used for detection and diagnosis of tumors or other abnormalities in the portion of the brain related to the auditory function. In general, a stimulus comprising a pulse of acoustic energy (characterized by an abrupt onset and decay, and of short duration), is directed against the tympanic membrane of the ear, and the resultant electric activity of the brain is recorded and evaluated. Commonly, a pathologically involved ear and auditory neurological pathway manifests a greater time interval (referred to as the latency) between the application of the stimulus and the electrical response of the brain stem. Abnormalities in both the morphology (waveshape) and temporal characteristics of the recorded electrical wave patterns are diagnostically significant.

Comparison of the latencies of the respective ears (with stimuli amplitude levels corrected for any conductive hearing loss) is referred to as "differential latency" of the subject.

The patient's response to the BSER stimulus is a very low level electrical voltage, typically on the order of 250 nV and must be extracted from a relatively noisy environment. The subject's body can accumulate a significant alternating current voltage at the frequency of utility power, e.g., 60 Hz and its harmonics. In addition, electrical connections must be made at the surface of the skin, introducing a significant electrical resistance. Accordingly, current BSER instruments are highly sophisticated and expensive equipment. Such instruments typically include special preamplifier circuits and employ microprocessors to accumulate many thousands of BSER responses, which are processed to distinguish the BSER wave pattern from normal background electrical noise. Such current BSER techniques, in addition to requiring expensive equipment, are also cumbersome and time consuming.

SUMMARY OF THE INVENTION

The present invention provides a simple screening device for performing differential latency evaluation to determine the necessity for more elaborate BSER evaluation. The present invention utilizes the ability of the human brain to locate a complex sound source, as, in effect, an internal self-processing mechanism for determining differential latency, which does not require the complex techniques for improving the signal to noise ratio.

In accordance with one aspect of the present invention, respective stimuli are applied to the ears of the subject. The stimulus applied to one ear is offset in time, either leading or lagging the stimulus applied to the other ear. It has been found that the stimuli are perceived by the subject as being generated by a sound source inside the subject's head, at a location within the head in accordance with the interaural differential latency. Accordingly, the time offset between the stimuli can be varied until the apparent source of the stimuli is perceived by the subject as being in the vicinity of a predetermined position (typically the center of the interior of the subject's head). It has been found that the time offset corresponding to a perception of the sound source as located in the center of the subject's head is indicative of the interaural differential latency of the subject.

BRIEF DESCRIPTION OF THE DRAWING

A preferred exemplary embodiment will hereinafter be described in conjunction with the appended drawing wherein like numerals denote like elements and:

FIGS. 2(A) and 2(B) is a block schematic diagram of the audiometer of FIG. 1; and FIG. 3 is a timing diagram of the control signals applied to the Latency Display block 30 shown in FIGS. 2(A) and 2(B).

DETAILED DESCRIPTION OF THE PREFERRED EXEMPLARY EMBODIMENT

Figure 1:
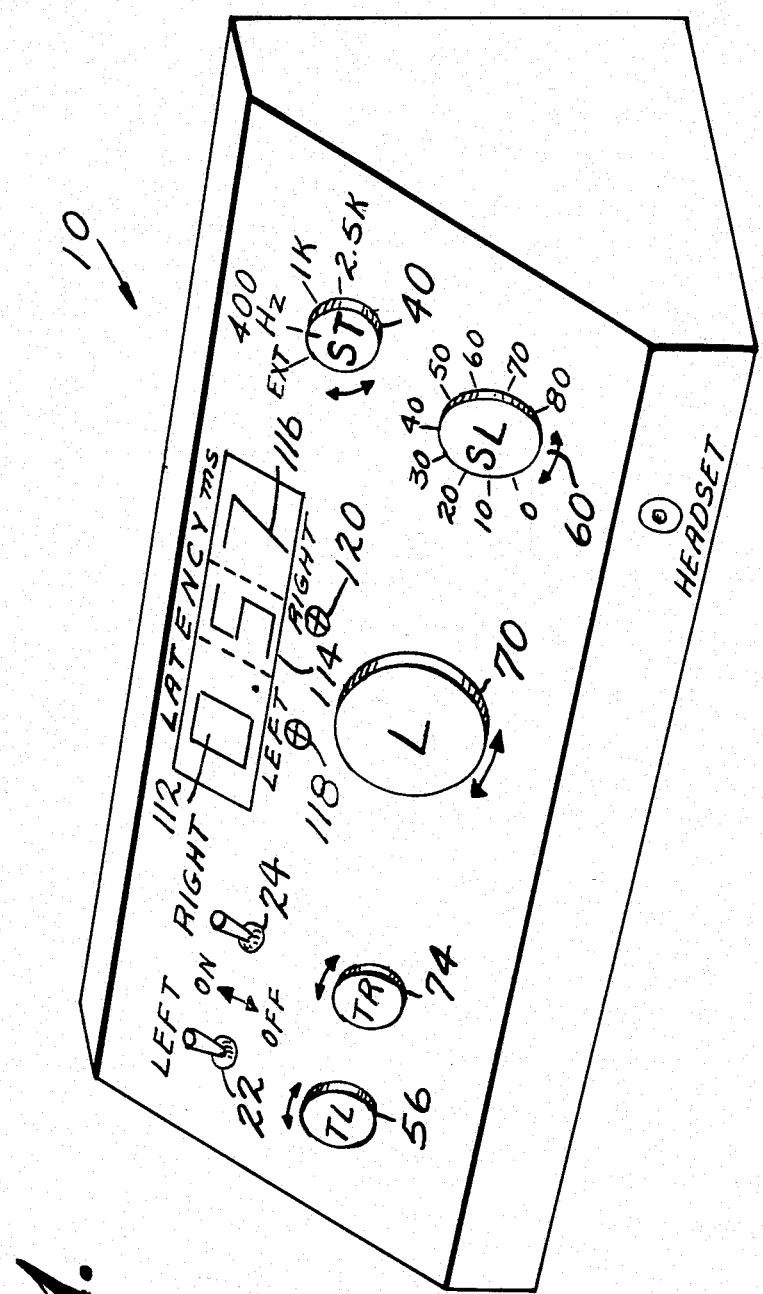
FIG. 1 is a pictorial illustration of a differential latency audiometer in accordance with the present invention.
Figure 2A:
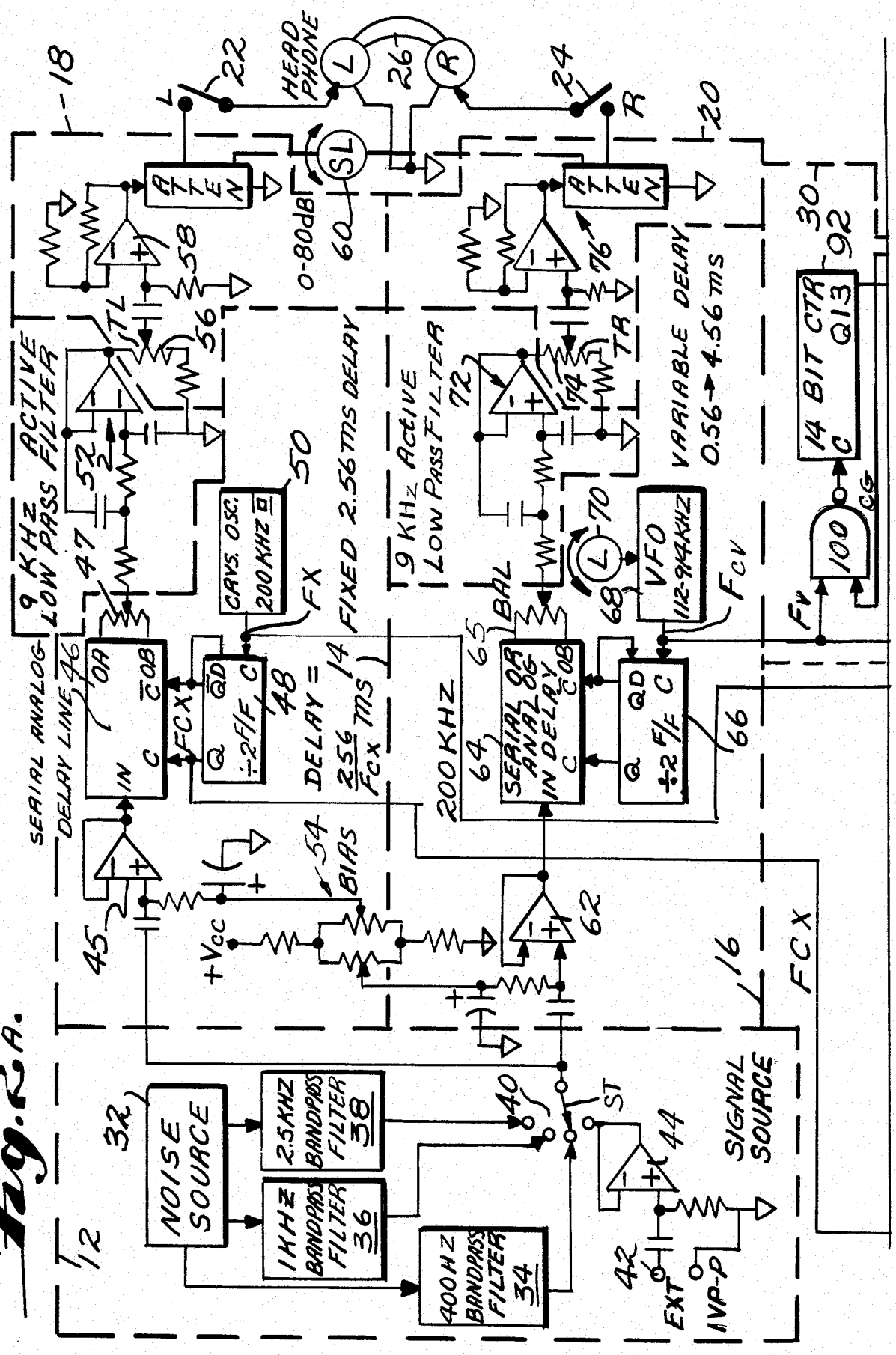

Referring to FIGS. 1 and 2, a differential latency audiometer 10, in accordance with the present invention, comprises an audiometric signal source 12, which supplies identical audiometric test signals to a fixed delay channel 14 and a variable delay channel 16. The respective delayed audiometric test signals are applied through attenuator circuits 18 and 20, and respective switches 22 and 24, to the respective transducers of a standard headphone 26. Fixed delay channel 14 also provides signals to suitable control logic 28, and to suitable latency derivation and display logic 30. Similarly, variable delay channel 16 provides signals to latency derivation and display logic 30.

Audiometric signal generator 12 provides an electrical signal (referred to herein as the audiometric test signal), preferably corresponding to a complex sound. The audiometric test signal is substantially continuous, and is to be distinguished from the short duration impulse stimuli used on conventional BSER apparatus. Signal generator 12 suitably comprises a digital noise source 32, such as a National Semiconductor MM5837. Noise source 32 generates a white noise output signal, which is applied to respective active filters 34, 36 and 38. Filters 34, 36 and 38 provide, in effect, individual octave-band souces centered at 400, 1,000 and 2,500 Hz. The outputs from filters 34, 36 and 38 are provided to respective pole terminals of a selector switch 40 (ST). An external source input connection 42 is also provided, coupled to a fourth terminal of selector switch 40 through a suitable buffering amplifier 44.

Filters 34, 36 and 38, in effect, provide three separate sources in different portions of the speech spectrum, and thus provide for comprehensive evaluation of the nature of the subject's differential latency. Additional flexibility is provided through external source input connection 42, through which signals from a recorder, radio, etc., may be utilized as the audiometric test signal.

The wiper of switch 40, and thus the selected audiometric test signal, is connected in parallel to fixed delay channel 14 and variable delay channel 16.

Fixed delay channel 14 suitably comprises a buffer amplifier 45, a clocked delay circuit 46 such as a RETICON SAD-512 charge-coupled "bucket brigade" serial analog delay line, a flip-flop 48, a crystal oscillator 50 providing a clock signal of frequency $F_x$ (suitably 200 kHz), and a suitable two-pole active low pass filter 52.

Delay element 46 suitably comprises two 256-stage sections of charge-coupled "bucket brigade", and provides outputs OA and OB in alternate half cycles of clock signals C, $\overline{C}$, of frequency $F_{cx}$, applied thereto. In response to each clock signal applied thereto, delay device 46 shifts the contents of each stage thereof into the next successive stage; the first stage receives indicia of the signal applied to the input terminal of the delay device, while the last stage of the device provides output signals OA and OB. A balance potentiometer 47 coupled across the OA and OB outputs, adjusts the relative amplitude of the two output components to minimize switching steps occurring at the $F_{cx}$ clock frequency.

Clock signals C and $\overline{C}$ are generated by flip-flop 48 and crystal oscillator 50. Flip-flop 48 is suitably a D-type flip-flop, connected with the D input tied to the $\overline{Q}$ output thereof to provide for toggle mode operation. Flip-flop 48 then operates as a "divide-by-two" divider. The signal ($F_x$) from crystal oscillator 50 is applied to the clock output of flip-flop 48. The Q, and $\overline{Q}$ outputs of flip-flop 48 are applied to the C and $\overline{C}$ inputs of delay device 46. Thus, delay device 46 has applied thereto a clock signal of frequency $F_{cx}=F_x/2$ (e.g., 100 kHz). As will hereinafter be explained in more detail, the 100 kHz signal ($F_{cx}$) provided at the Q output of flip-flop 48 is also provided to control logic 28 and the output of crystal oscillator 50 ($F_x$) is applied to latency derivation and display logic 30.

The selected audiometric test signal is applied through a suitable coupling capacitor, e.g., 0.10 microfarad, to buffer amplifier 45. Buffer amplifier 45 combines the audiometric test signal with a bias voltage provided by a bias source circuit 54 (common to both fixed delay channel 14 and variable delay channel 16). The output of buffer amplifier 45 is applied to the input terminal of clocked delay element 46.

The output of clocked delay line 46, as provided at potentiometer 47, is applied to low pass filter 52. Low pass filter 52 suitably rejects frequency components above 9 kHz at $-12$ DB/octave, and suppresses any switching transients in the delay line output signal. The output signal of low pass filter 52 is thus an accurate replication of the original audiometric test signal provided by source 12, delayed by a predetermined amount, e.g., 2.56 ms.

The output of low pass filter 52 is applied to adjustment attentuator 18. More specifically, the output of the low pass filter 52 is applied across a variable "threshold left" (TL) potentiometer 56. Potentiometer 56 is used to adjust the amplitude of the test signal to compensate, if necessary, for any conductive hearing loss in the associated (e.g., left) ear. The amplitude adjusted signal is then applied through an 80 DB step attenuator 58 (and switch 22) to the associated (e.g., left) transducer of head set 26. As will be explained, step attenuator 58 is adjusted in tandem with a corresponding attenuator (76) in variable delay channel 16 by a "sound level" (SL) control mechanism 60 to adjust the overall amplitude level of the stimuli.

Variable delay channel 16 is substantially similar to fixed delay channel 14, with the exception that variable clocking provisions for the delay element are included. The audiometric test signal from source 12 is applied (through a suitable coupling capacitor) to a buffer amplifier (corresponding to buffer amplifier 45) which combines the bias voltage from bias supply 54 and the audiometric test signal. The output of buffer amplifier 62 is applied to the input of a serial delay element 64, substantialy identical to delay element 46. Delay element 66, however, is driven by a clock signal of variable frequency $F_{cv}$.

The C and $\overline{C}$ clock signals at frequency ($F_{cv}$) for driving (stepping) delay element 64 are provided by a divide-by-two flip-flop 66, similar to flip-flop 48, and a variable frequency oscillator 66. Divide-by-two flip-flop 66 is driven by variable frequency oscillator 68, which provides a clock signal to flip-flop 66 having a frequency ($F_v$) which varies over a predetermined range, e.g., from 112 kHz to 914 kHz, set by a "latency" (L) control knob 70. The range of frequency of $F_v$ suitably extends both above and below the fixed frequency $F_x$, to allow the variable delay channel stimulus to either lead or lag the fixed delay channel stimulus. The output signal ($F_v$) of variable frequency oscillator 68 is also applied to latency derivation and display logic 30, as will hereinafter be more fully explained.

The output of delay line 64 is applied through a low pass filter 72 (corresponding to filter 52). A balancing potentiometer 65 and low pass filter 72 filter out switch transients in the output of the delay line, to provide an accurate reproduction of the selected audiometric test signal from source 12, delayed by an amount inversely proportional to the clock frequency ($F_{cv}$) applied to delay line 64.

The output of filter 72 is applied across a "threshold right" (TR) potentiometer 74 (corresponding to TL potentiometer 56) which is utilized to adjust for conductive hearing loss in the right ear. The amplitude adjusted signal is then applied through an 80 DB step-down attenuator 76 (corresponding to and operated in tandem with attenuator 58) and switch 24 to the right transducer of earphones 26.

Control logic 28, establishes system timing in synchrony with the crystal controlled frequency clock signal ($F_{cx}$) of fixed delay channel 14. Clock signal $F_{cx}$ is applied as an input to a 14-bit counter 78. The seven most significant output bits of counter 78 are applied to suitable logic for generating respective signals RE (reset), SC (start calculation), and LE (latch enable), which are utilized to control the operation of the latency derivation and display logic 30. More specifically, the seven most significant output bits, Q8–Q14, of counter 78 are applied to the respective input terminals of an eight-input AND gate 80 (the eighth input of which is tied high). The output of AND gate 80 is a pulse (p), 1.28 ms in duration and repeating each 163.84 ms where $F_{cx}$ is 100 kHz. Pulse P is applied as a clock signal to a divider comprising two cascaded D-type flip-flops 82 and 84, each with $\overline{Q}$ output connected to D input for toggle mode operation.

The Q outputs of flip-flops 82 and 84 are connected to respective input terminals of a three-input AND gate 86. The third input of AND gate 86 is receptive of pulse P from AND gate 80. The output of AND gate 86 provides reset pulse RE, 1.28 ms in duration, repeating each 655.36 ms.

The $\overline{Q}$ output of flip-flop 82 and the Q output of flip-flop 84 are applied to respective input terminals of a further three-input AND gate 88. The third input of AND gate 88 is receptive of the P pulse from AND gate 80. AND gate 88 generates an SC pulse, 1.28 ms in duration, occurring 163.84 ms after the occurrence of each reset pulse, RE.

The $\overline{Q}$ output of flip-flop 82, and the $\overline{Q}$ output of AND gate 84 are applied to two respective inputs of a three-input NAND gate 90. The third input of NAND gate 90 is receptive of the pulse P from AND gate 80. NAND gate 90 provides a negative going pulse, LE, 1.28 ms in duration occurring 491.52 ms after each reset pulse, RE. As will hereinafter be explained, the control pulses RE, SC and LE are utilized to control latency derivation and display logic 30.

Latency derivation and display logic 30, in effect, derives the interaural differential latency, and an indication of which ear is most latent, from the frequencies of oscillators 50 and 68. Latency derivation display logic 30 comprises respective 14-bit counters 92 and 94, a suitable memory device 96, a D-type flip-flop 98, respective two-input NAND gates 100 and 102, a two-input AND gate 104, three BCD seven-segment latch and decoder drivers 106, 108, and 110, three seven-segment LED digital displays 112, 114, and 116, and respective LED's 118 and 120, with associated driving amplifiers 122 and 124.

NAND gate 100, AND gate 104 and flip-flop 98, cooperate with counter 92 to provide a signal indicative of a time period corresponding to a predetermined number of cycles of the variable frequency ($F_v$) clock signal from oscillator 68.

The variable frequency signal ($F_v$) from variable frequency oscillator 68 is applied to respective inputs of NAND gate 100 and AND gate 104. The second input of NAND gate 100 is coupled to the $\overline{Q}$ output of flip-flop 98, as will be explained. The second input of AND gate 104 is receptive of the SC control signal from AND gate 88 in control logic 28. The output of NAND gate 100 is applied to the clock input of counter 92. The thirteenth output (Q13) of counter 92 is applied as the clock signal to flip-flop 98. Flip-flop 98 is suitably a D-type flip-flop with $\overline{Q}$ output coupled to D input to operate in a toggle mode. The output of AND gate 104 is connected to the reset terminal of flip-flop 98. The $\overline{Q}$ output of flip-flop 98 provides a "count gate" signal (CG) which is, as previously noted, fed back to the second input of NAND gate 100. Thus, the SC control signal resets flip-flop 98, to enable NAND gate 100 with respect to the $F_v$ signal, and, accordingly initiate the count in counter 92. The count continues to accumulate until flip-flop 98 is clocked by the Q13 output of counter 92, causing CG to go low and disabling gate 100. It should be noted that the CG signal is of high value for a period equal to the predetermined number of cycles of $F_v$.

AND gate 102 and counter 94 cooperate to develop a count indicative of the number of cycles of the fixed frequency ($F_x$) clock signal generated by crystal oscillator 50 in fixed delay channel 14, that occur during the predetermined number of cycles of the variable frequency signal. The CG signal from flip-flop 98 is also applied as one input to NAND gate 102. The other input to NAND gate 102 is the output signal ($F_x$) from crystal oscillator 90 in fixed delay channel 14. The output of NAND gate 102 is applied as a clock input to 14-bit counter 94. The reset terminal of counter 94 is receptive of the reset control signal from AND gate 86 in control logic 28. The nine most significant bits representing a value $N_9$ are applied to the address lines of memory device 96.

In operation, the reset pulse RE generated by AND gate 86 in control logic 28 initially resets fixed frequency counter 94 to logic zero. The next succeeding SC pulse (occurring 163.82 ms after the RE pulse) enables AND gate 104 so that the next positive-going transition in the variable frequency ($F_v$) clock signal resets flip-flop 98. The $\overline{Q}$ output (signal CG) is thus forced high, concurrently enabling NAND gate 100 with respect to the variable frequency signal $F_v$ and NAND gate 102 with respect to the fixed frequency clock signal $F_x$. Accordingly, the $F_v$ clock pulses begin to increment variable frequency counter 92 and the $F_x$ clock pulse increment counter 94. Counter 92 continues to be incremented until a positive-going transition in generated at the thirteenth stage output (Q 13), i.e., 8192 $F_v$ pulses later. The positive-going transition Q 13 clocks flip-flop 98, causing the $\overline{Q}$ output thereof (signal CG) to go low, inhibiting NAND gates 100 and 102, and establishing the value of the count in counter 94.

The count in fixed frequency counter 94 is thus indicative of the variable frequency setting. Specifically, the duration of the count gate (CG) signal is equal to 8192 /$F_v$ ms, varying from 8.96 to 72.96 ms in accordance with the setting of the frequency $F_v$ within the frequency range of 112 kHz to 914 kHz. Accordingly, the count accumulated by counter 94 is equal to the number of $F_x$ pulses generated during the count gate (CG) interval. The nine most significant output bits (Q6–Q14) of counter 94, having value $N_9$, are representative of the differential latency information.

The binary outputs Q6–Q14 of counter 94 provide an address control signal to memory 96. Memory device 96 is suitably a 1024×16 programmable read only memory (PROM). PROM 96 includes respective locations corresponding to the various differential latencies over a predetermined range. The locations contain the appropriate control signals corresponding to the latency for driving the LED's 118 and 120 and seven-segment displays 112, 114, and 116.

The contents of the location designated by value $N_9$ are applied to latches 106, 108 and 110 and driving amplifiers 122 through 124 to appropriately drive seven-segment display elements 112, 114 and 116 and left or right ear indicator LED's 118 and 120. The following Table I shows the interrelationship between exemplary frequencies $F_v$ over the range of approximately 112 kHz to 914 kHz, the duration of the count gate (CG), the decimal equivalent of the contents ($N_9$) of counter 98, and the differential latency (with the fixed frequency being equal to 200 kHz resulting in a fixed delay of 2.56 ms).

TABLE I

| $F_v$ kHz | $F_{cv}$ kHz | Right Channel Delay ($D_r$) ms | The Differential Latency ($D_1 - D_r$) ms | Count Gate Period (CG), ms | Decimal Equivalent of $N_9$ | Display |
|---|---|---|---|---|---|---|
| 914.28 | 457.14 | 0.56 | +2.00 | 8.96 | 56 | R 200 |
| 328.20 | 164.10 | 1.56 | +1.00 | 24.96 | 156 | R 100 |
| 200.00 | 100.00 | 2.56 | 0.00 | 40.96 | 256 | 0.00 |
| 143.82 | 71.91 | 3.56 | −1.00 | 56.96 | 356 | L 1.00 |
| 112.28 | 56.14 | 4.56 | −2.00 | 72.96 | 456 | L 2.00 |

It should be appreciated that Table I is not intended to be complete, but rather provides exemplary values only. PROM 96 would include a location corresponding to each unique value of $N_9$, each containing indicia of the differential latency corresponding to such count, i.e., the appropriate control signals to generate the corresponding display.

The outputs of counter 94 are stable within less than 80 ms after the occurrence of the SC control pulse. Accordingly, upon generation of the LE control pulse by NAND gate 90 in control logic 28 (491.52 ms after the reset pulse), the BCD outputs of PROM 96 are latched into the BCD seven-segment latch/decoder drivers 106, 108 and 110. These in turn drive seven-segment display elements 112, 114 and 116 and the left and right indicator LED's 118 and 120.

In use, the operator places headset 26 on the subject's ear. Headset 26 suitably is coded, i.e., right transducer colored red, to ensure that the proper transducer is placed with the proper ear. The stimulus sound level (SL) attenuator 60 is then set to zero and the right earphone switch 24 non-conductive (off). The stimulus switch (ST) 40 is then set to the desired audiometric test signal, e.g., the 400 Hz noise signal from filter 34. Thereafter, the left threshold (TL) compensator potentiometer 56 is increased until the subject just reliably hears the stimulus. Next, the left earphone switch 22 is rendered non-conductive (set to off) and right earphone switch 24 rendered conductive (set to on). The right threshold compensator potentiometer (TR) 74 is then set in a manner similar to potentiometer 56. After both left and right thresholds have been set using potentiometers 56 and 74, both earphone switches are turned on, and the tandem sound level (SL) attenuator 60 is increased to a desired level. The operator would then instruct the subject by demonstrating the movement of the preceived "sound image" (the apparent source of the stimulus). This is accomplished by varying latency control (L) 70, i.e., varying the frequency $F_v$.

After familiarizing the subject with the phenomena of the perceived sound image (typically taking less than one minute), the subject is requested to adjust the latency (L) control 70 until the sound image is perceived as being located in the center of the subject's head. The latency display is then read and the results recorded. After ten or more trials, the test is concluded or test conditions changed and the test repeated. It has been found that a test sequence of ten trials seldom requires more than five minutes to complete, including the instruction period.

The average latency time and standard deviation of the measurements are calculated from the ten trials. A standard deviation of 0.05 ms or less indicates satisfactory tests. If the average differential latency is less than ±0.10 ms, for the ten trial tests, the differential latency of subject is within the normal range. However, detection of a differential latency greater than 0.20 ms suggests that more comprehensive BSER evaluation is warranted.

It will be understood that while various of the connections between the elements are shown in the drawing as single lines, they are not so shown in a limiting sense and may comprise plural connections as is understood in the art. Further, the above description is of a preferred exemplary embodiment of the present invention, and the invention is not limited to the species form shown. Modifications may be made in the design and arrangement of the elements without departing from the spirit of the invention as expressed in the appended claims.

What is claimed is:

1. A method for determining the differential interaural latency of a subject comprising the steps of:
    applying a first complex sound signal to a first ear of said subject;
    applying, simultaneously with the application of said first signal, a second complex sound signal to the second ear of said subject, said second sound signal corresponding to said first sound signal, but offset in time with respect to said first sound signal;
    varying the time offset of said second signal until the apparent source of said sounds is perceived by said subject as in the vicinity of a predetermined position within the interior of said subject's head; and
    deriving indicia of differential interaural latency from said varied time offset.

2. The method of claim 1 wherein:
    said applying a first sound signal step comprises the steps of generating a complex sound test signal and applying said test signal to a first clocked delay line driven at a predetermined first frequency to produce said first sound signal;
    said applying said second sound signal step comprises the steps of applying said test signal to a second clocked delay line driven at a variable second frequency to produce said second sound signal; and
    said varying said time offset step comprises the step of varying said second frequency.

3. The method of claim 2 wherein said deriving step comprises generating from signals indicative of said first and second frequencies a count indicative of said differential latency.

4. The method of claim 3 further including the step of displaying indicia of said differential interaural latency.

5. The method of claim 1 wherein said predetermined position is the center of said subject's head.

6. The method of claim 5 further including the step of displaying indicia of said differential interaural latency.

7. A method as in claim 1 wherein said first complex sound signal applying step includes the step of producing a wide spectrum noise signal.

8. A method as in claim 7 wherein said first complex sound signal applying step further includes the step of filtering said wide spectrum noise signal.

9. A method as in claim 8 wherein said filtering step comprises the step of extracting a selected one of a plurality of signals from said wide spectrum noise signal, each of said plurality of extracted signals being in a different portion of the audible spectrum.

10. A method as in claim 1 wherein:
    said first complex sound signal applying step continuously generates said first signal; and
    said second sound signal applying step continuously generates said second signal.

11. A method as in claim 1 wherein said first sound signal applying step includes the step of frequency filtering said first complex sound signal.

12. A method as in claim 2 further including the steps of:
    dividing a constant by said second frequency to produce a time interval;
    counting the number of alternations of said first frequency occurring during said time interval; and
    locking up, in a storage device, indicia of differential interaural latency corresponding to said count.

13. A method as in claim 12 further including the step of displaying said indicia.

14. Apparatus for determining the difference in latency between application of a stimulus to the respective ears of a subject and the electrical response of the brain stem comprising:
    means for generating a first complex test signal;
    means for generating, simultaneously with the generation of said first signal, a second complex test signal corresponding to said first test signal, but time-shifted with respect thereto;

transducer means, responsive to said first and second test signals, for applying audio stimuli corresponding to said first and second test signals to the first and second ears of said subject;

means for varying the time-shift between said first and second test signal; and means for generating indicia of said time-shift, whereby the time-shift corresponding to a predetermined perception of said stimuli by said subject can be determined.

15. The apparatus of claim 14 wherein:
said means for generating a first test signal comprises:
fixed delay means, responsive to an audiometric test signal, for delaying said audiometric test signal by a fixed amount of time; and
said means for generating said second test signal comprises variable delay means, responsive to said audiometric test signal, for delaying said audiometric test signal by a variable amount of time, over a range of times.

16. The apparatus of claim 15 wherein said range of times encompasses said fixed amount of time.

17. An apparatus as in claim 14 wherein said first test signal generating means includes means for producing a wide spectrum noise signal.

18. An apparatus as in claim 17 wherein said first test signal generating means further includes means for filtering said wide spectrum noise signal.

19. An apparatus as in claim 18 wherein said filtering means includes means for extracting a selected one of a plurality of signals from said wide spectrum noise signal, each of said plurality of extracted signals being in a different portion of the audible spectrum.

20. An apparatus as in claim 14 wherein said first test signal generating means includes means for frequency filtering said first complex test signal.

21. An apparatus as in claim 14 wherein:
said first test signal generating means continuously generates said first test signal; and
said second test signal generating means continuously generates said second test signal.

22. An audiometer comprising:
first delay means, responsive to an audiometric test signal applied thereto, for generating a first test signal corresponding to said audiometric test signal delayed in time by a first delay time;
second delay means, responsive to said audiometric test signal, for generating, simultaneously with the generation of said first test signal, a second test signal corresponding to said audiometric test signal delayed in time by a second delay time;
means for varying said second delay time;
means for converting said first and second test signals into first and second aural stimuli for the respective ears of a subject; and
means for generating indicia of the difference between said first and second time delay, whereby the difference between said first and second time delay corresponding to predetermined perceptions by said subject of said first and second stimuli can be determined.

23. An audiometer as in claim 22 further including means for filtering said audiometric test signal, said first and second delay means responsive to said filtered audiometric test signal.

24. An audiometer as in claim 23 wherein said filtering means includes means for extracting a selected one of a plurality of signals from said audiometric test signal, each of said plurality of extracted signals being in a different portion of the audible spectrum.

25. An apparatus as in claim 22 wherein:
said first delay means continuously generates said first test signal; and
said second delay means continuously generates said second test signal.

26. The audiometer of claim 22 wherein:
said first delay means comprises a first clocked delay line, responsive to a first clock signal applied thereto;
said second delay means comprises a second clocked delay line, responsive to a second clock signal applied thereto; and
said means for varying said second delay time comprises a variable frequency oscillator for controllably generating said second clock signal to said second clocked delay line.

27. An audiometer as in claim 26 wherein said indicia generating means comprises:
means for dividing a constant by the frequency of said second clock signal to produce a time interval;
means for counting the number of alternations of said first clock signal occurring during said time interval; and
storage means, responsive to said count produced by said counting means, for producing said indicia of differential interaural latency.

28. The audiometer of claim 26 wherein:
said means for generating indicia comprises logic means, responsive to signals indicative of said first and second clock signals for generating a count indiciative of the difference between said first and second delay times; and
memory means, responsive to said count, for generating indicia of the differential interaural latency of said subject.

29. An audiometer as in claim 28 wherein said logic means comprises:
means for dividing a constant by the frequency of said second clock signal to produce a time interval; and
means for counting the number of alternations of said first clock signal occurring during said time interval to produce said count.

30. The audiometer of claim 26 wherein said variable frequency oscillator is capable of varying said second clock signal over a range of frequencies extending from below the frequency of said first clock signal to above the frequency of said first clock signal.

31. The audiometer of claim 28 wherein said variable frequency oscillator is capable of varying said second clock signal over a range of frequencies extending from below the frequency of said first clock signal to above the frequency of said first clock signal.

32. The audiometer of claim 31 further including means for generating said audiometric test signal.

33. The audiometer of claim 30 further including means for generating said audiometric test signal.

34. The audiometer of claim 28 further including means for generating said audiometric test signal.

35. The audiometer of claim 26 further including means for generating said audiometric test signal.

36. The audiometer of claim 22 further including means for generating said audiometric test signal.

37. The audiometer of claim 22 wherein said converting means includes transducer means for converting said first and second test signals into said first and second aural stimuli.

38. An audiometer as in claim 35 wherein said audiometric test signal generating means comprises means for producing a complex sound.

39. An audiometer as in claim 35 wherein said audiometric test signal generating means comprises means for producing wide spectrum noise.

40. An audiometer as in claim 36 wherein said audiometric test signal generating means comprises means for producing a complex sound.

41. An audiometer as in claim 36 wherein said audiometric test signal generating means comprises means for producing wide spectrum noise.

* * * * *